United States Patent [19]

Gershengorn et al.

[11] Patent Number: 5,288,621
[45] Date of Patent: Feb. 22, 1994

[54] PITUITARY TRH RECEPTOR

[75] Inventors: Marvin C. Gershengorn; Richard E. Straub, both of New York, N.Y.

[73] Assignee: Cornell Research Foundation, Inc., Ithaca, N.Y.

[21] Appl. No.: 629,104

[22] Filed: Dec. 14, 1990

[51] Int. Cl.[5] .............................. C07K 13/00
[52] U.S. Cl. ........................ 435/69.4; 536/23.51; 530/399
[58] Field of Search ............... 435/69.4; 536/23.51; 530/350, 399

[56] References Cited

PUBLICATIONS

Oron et al. 1987 Molecular Endocrinology 1:918–925.
Phillips & Hinkle 1989, Molecular Pharmacology 35:533–540.
Straub et al. 1989, Molecular Endocrinology 3:907–914.
Gershengorn et al. 1990, J. Exp. Zool. (Supp.) 4:78–83.

*Primary Examiner*—Robert J. Hill, Jr.
*Assistant Examiner*—Karen C. Carlson
*Attorney, Agent, or Firm*—Yahwak & Associates

[57] ABSTRACT

Disclosed for the first time is the isolation, sequence, and expression cloning of a cDNA encoding for pituitary thyrotropin-releasing hormone receptor, as well as the amino acid sequence for the receptor per se.

3 Claims, 4 Drawing Sheets

FIG. 1A
TRH ↓
FIG. 1B
TRH ↓
FIG. 1C
TRH ↓
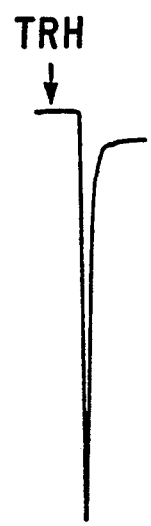
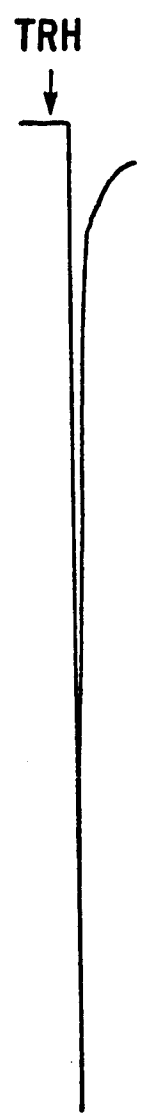
500 nA | 1 min

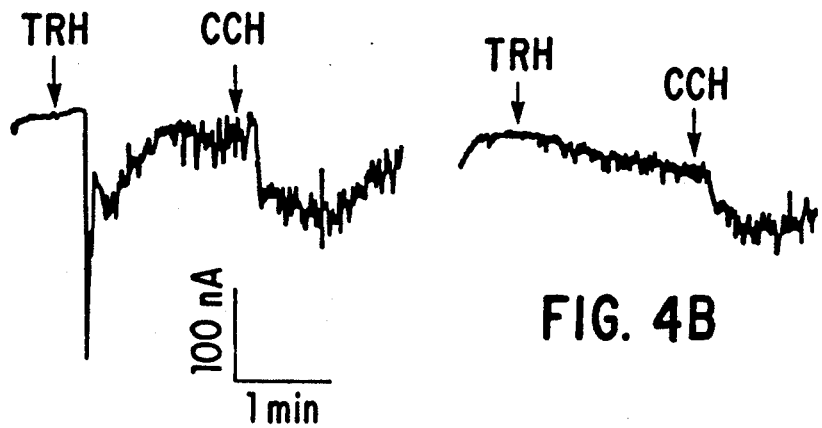
FIG. 4A
FIG. 4B
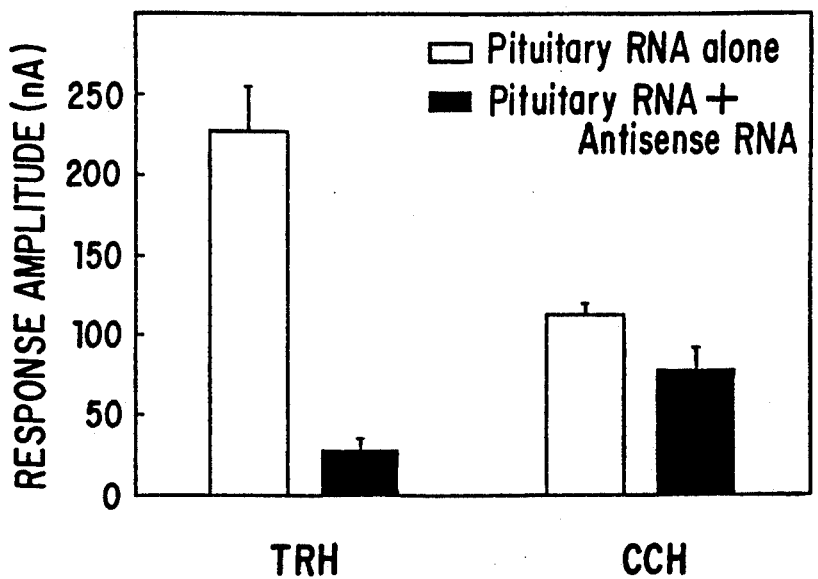
FIG. 5

SEQUENCE LISTING ( 1 ) GENERAL INFORMATION:

( i i i ) NUMBER OF SEQUENCES: 3

( 2 ) INFORMATION FOR SEQ ID NO: 1 :

( i ) SEQUENCE CHARACTERISTICS:
        ( A ) LENGTH: 1752 base pairs
        ( B ) TYPE: nucleic acid
        ( C ) STRANDEDNESS: single
        ( D ) TOPOLOGY: linear ( i i ) MOLECULE TYPE: DNA (cDNA)

( x i ) SEQUENCE DESCRIPTION: SEQ ID NO:1:

```
GAATTCCGGA  GGGTTTAGAG  GAACTGCCGC  TCTGAAGACT  GAGCCTCTGC        50

TAAGTGATCT  TCCTGCCAGA  CAGACTGGAC  AAGATTTCTT  CTGCAGGATT       100

GGAAACTTGG  ACCTATTAGC  ACTTCATCTA  CCAGAGAAAC  AGGCAGCGTG       150

ACAGAGTGAA  GAGGGGAAAG  AACTACTGCA  AAAACAAACA  GACAGAAAGG       200

TGAAGGCTGG  AAAGATGTTT  TAGAGTCCCC  GTGTCAGAGA  AGCTTCAAGC       250

CACTGAAG        ATG GAG AAT GAT ACT GTC AGT GAA ATG AAC CAA      291

ACC GAG CTC CAG CCA CAA GCA GCT GTG GCC CTC GAG TAC CAG          333
GTG GTT ACC ATC TTA CTT GTG GTC ATT ATT TGT GGA CTG GGC          375
ATT GTG GGC AAC ATC ATG GTA GTC GTG CTG ATG AGA ACA              417
AAG CAC ATG AGA ACC CCT ACA AAC TGT· TAC CTG GTA AGT CTG         459
GCT GTG GCA GAT CTC ATG GTT CTG GTG GCT GCA GGA CTC CCC          501
```

```
AAC ATA ACC GAC AGT ATC TAT GGT TCC TGG GTC TAT GGC TAT      543
GTT GGC TGC CTC TGC ATT ACA TAT CTC CAG TAC CTA GGC ATT      585
AAT GCA TCT TCA TGT TCA ATA ACG GCC TTT ACC ATT GAA AGG      627
TAC ATA GCA ATC TGT CAC CCC ATC AAA GCC CAG TTT CTC TGC      669
ACG TTT TCC AGA GCC AAA AAA ATC ATC ATC TTT GTC TGG GCC      711
TTC ACA TCC ATT TAC TGT ATG CTC TGG TTC TTC CTG CTG GAT      753
CTC AAC ATC AGC ACC TAC AAA AAC GCT GTT GTG GTT TCC TGT      795
GGC TAC AAG ATC TCC AGG AAC TAC TAC TCA CCT ATT TAC CTA      837
ATG GAC TTT GGT GTC TTT TAT GTT GTG CCA ATG ATC CTG GCC      879
ACT GTG CTT TAT GGA TTT ATA GCT AGA ATC CTC TTC TTA AAC      921
CCC ATT CCT TCA GAC CCT AAA GAA AAC TCT AAG ATG TGG AAA      963
AAT GAC TCA ATC CAT CAG AAC AAG AAT TTG AAT TTA AAT GCC     1005
ACC AAC AGA TGC TTC AAC AGC ACT GTA TCT TCC AGG AAG CAG     1047
GTC ACC AAG ATG CTC GCA GTG GTT GTA ATT CTG TTT GCC CTT     1089
TTA TGG ATG CCC TAC AGG ACT CTT GTG GTT GTC AAC TCA TTT     1131
CTC TCC AGC CCT TTC CAG GAA AAT TGG TTC TTG CTC TTT TGC     1173
AGA ATT TGC ATT TAT CTC AAC AGT GCC ATC AAC CCA GTG ATT     1215
TAC AAC CTC ATG TCT CAG AAA TTT CGT GCA GCC TTC AGG AAG     1257
CTC TGC AAT TGC AAG CAG AAG CCC ACA GAA AAA GCT GCT AAC     1299
TAC AGT GTG GCC CTA AAT TAC AGT GTC ATC AAG GAG TCA GAC     1341
CGC TTC AGC ACA GAG CTA GAA GAT ATC ACC GTC ACC GAT ACG     1383
TAT GTG TCA ACC ACA AAA GTG TCC TTT GAT GAC ACC TGC TTG     1425
GCC TCT GAG AAC TAA     AGAAGGCCAT AAAGAACCCT ATAATGTTCT     1470
TCATGTATAT TTATTTCATA ATTATGATCT TCATCAAATA ATTCAGCAAC     1520

AGATGTCTTC AGGCAAGTTA CATACTGGGA AGCAGTTCAC TATTAAGATT     1570

TTCAGCAACT TACGGACTAC ATCAAGTGAC AAGTTTAACC TATGGTGTGA     1620

GAACTTAATT CAAAACTCAA ATAATCTTCT TTGACAAGAG TGATCATGGA     1670

TAAAAATGGA CTCAGTTCTT GTGCATATAG CTTTTCTTTG ACTGCCAAAC     1720

AAGAGCGAAT ATGAACTTCC ATCTTGAACT GG                        1752
```

( 2 ) INFORMATION FOR SEQ ID NO:2 :

( i ) SEQUENCE CHARACTERISTICS:
        ( A ) LENGTH: 1182 base pairs
        ( B ) TYPE: nucleic acid
        ( C ) STRANDEDNESS: single
        ( D ) TOPOLOGY: linear ( i i ) MOLECULE TYPE: DNA (cDNA)

( x i ) SEQUENCE DESCRIPTION: SEQ ID NO:2:

```
ATG GAG AAT GAT ACT GTC AGT GAA ATG AAC CAA ACC GAG           39
CTC CAG CCA CAA GCA GCT GTG GCC CTC GAG TAC CAG GTG           78
GTT ACC ATC TTA CTT GTG GTC ATT ATT TGT GGA CTG GGC          117
ATT GTG GGC AAC ATC ATG GTA GTC CTG GTG GTC ATG AGA          156
ACA AAG CAC ATG AGA ACC CCT ACA AAC TGT TAC CTG GTA          195
AGT CTG GCT GTG GCA GAT CTC ATG GTT CTG GTG GCT GCA          234
GGA CTC CCC AAC ATA ACC GAC AGT ATC TAT GGT TCC TGG          273
GTC TAT GGC TAT GTT GGC TGC CTC TGC ATT ACA TAT CTC          312
CAG TAC CTA GGC ATT AAT GCA TCT TCA TGT TCA ATA ACG          351
GCC TTT ACC ATT GAA AGG TAC ATA GCA TCT CAC CCC               390
ATC AAA GCC CAG TTT CTC TGC ACG TTT TCC AGA GCC AAA          429
AAA ATC ATC ATC TTT GTC TGG GCC TTC ACA TCC ATT TAC          468
TGT ATG CTC TGG TTC TTC CTG CTG GAT CTC AAC ATC AGC          507
ACC TAC AAA AAC GCT GTT GTG GTT TCC TGT GGC TAC AAG          546
ATC TCC AGG AAC TAC TAC TCA CCT ATT TAC CTA ATG GAC          585
TTT GGT GTC TTT TAT GTT GTG CCA ATG ATC CTG GCC ACT          624
GTG CTT TAT GGA TTT ATA GCT AGA ATC CTC TTC TTA AAC          663
CCC ATT CCT TCA GAC CCT AAA GAA AAC TCT AAG ATG TGG          702
AAA AAT GAC TCA ATC CAT CAG AAC AAG AAT TTG AAT TTA          741
AAT GCC ACC AAC AGA TGC TTC AAC AGC ACT GTA TCT TCC          780
AGG AAG CAG GTC ACC AAG ATG CTC GCA GTG GTT GTA ATT          819
CTG TTT GCC CTT TTA TGG ATG CCC TAC AGG ACT CTT GTG          858
GTT GTC AAC TCA TTT CTC TCC AGC CCT TTC CAG GAA AAT          897
TGG TTC TTG CTC TTT TGC AGA ATT TGC ATT TAT CTC AAC          936
AGT GCC ATC AAC CCA GTG ATT TAC AAC CTC ATG TCT CAG          975
AAA TTT CGT GCA GCC TTC AGG AAG CTC TGC AAT TGC AAG         1014
CAG AAG CCC ACA GAA AAA GCT GCT AAC TAC AGT GTG GCC         1053
CTA AAT TAC AGT GTC ATC AAG GAG TCA GAC CGC TTC AGC         1092
ACA GAG CTA GAA GAT ATC ACC GTC ACC GAT ACG TAT GTG         1131
TCA ACC ACA AAA GTG TCC TTT GAT GAC ACC TGC TTG GCC         1170
TCT GAG AAC TAA                                             1182
```

( 2 ) INFORMATION FOR SEQ ID NO:3:

(i) SEQUENCE CHARACTERISTICS:
 (A) LENGTH: 393 amino acids
 (B) TYPE: amino acid
 (D) TOPOLOGY: linear (ii) MOLECULE TYPE: peptide (xi) SEQUENCE DESCRIPTION: SEQ ID NO:3:

```
Met Glu Asn Asp Thr Val Ser Glu Met Asn Gln Thr Glu Leu Gln
 1               5                  10                  15

Pro Gln Ala Ala Val Ala Leu Glu Tyr Gln Val Val Thr Ile Leu
                20                  25                  30

Leu Val Val Ile Ile Cys Gly Leu Gly Ile Val Gly Asn Ile Met
                35                  40                  45

Val Val Leu Val Val Met Arg Thr Lys His Met Arg Thr Pro Thr
                50                  55                  60

Asn Cys Tyr Leu Val Ser Leu Ala Val Ala Asp Leu Met Val Leu
                65                  70                  75

Val Ala Ala Gly Leu Pro Asn Ile Thr Asp Ser Ile Tyr Gly Ser
                80                  85                  90

Trp Val Tyr Gly Tyr Val Gly Cys Leu Cys Ile Thr Tyr Leu Gln
                95                  100                 105

Tyr Leu Gly Ile Asn Ala Ser Ser Cys Ser Ile Thr Ala Phe Thr
                110                 115                 120

Ile Glu Arg Tyr Ile Ala Ile Cys His Pro Ile Lys Ala Gln Phe
                125                 130                 135

Leu Cys Thr Phe Ser Arg Ala Lys Lys Ile Ile Ile Phe Val Trp
                140                 145                 150

Ala Phe Thr Ser Ile Tyr Cys Met Leu Trp Phe Phe Leu Leu Asp
                155                 160                 165

Leu Asn Ile Ser Thr Tyr Lys Asn Ala Val Val Val Ser Cys Gly
                170                 175                 180

Tyr Lys Ile Ser Arg Asn Tyr Tyr Ser Pro Ile Tyr Leu Met Asp
                185                 190                 195

Phe Gly Val Phe Tyr Val Val Pro Met Ile Leu Ala Thr Val Leu
                200                 205                 210

Tyr Gly Phe Ile Ala Arg Ile Leu Phe Leu Asn Pro Ile Pro Ser
                215                 220                 225

Asp Pro Lys Glu Asn Ser Lys Met Trp Lys Asn Asp Ser Ile His
                230                 235                 240

Gln Asn Lys Asn Leu Asn Leu Asn Ala Thr Asn Arg Cys Phe Asn
                245                 250                 255

Ser Thr Val Ser Ser Arg Lys Gln Val Thr Lys Met Leu Ala Val
                260                 265                 270

Val Val Ile Leu Phe Ala Leu Leu Trp Met Pro Tyr Arg Thr Leu
                275                 280                 285

Val Val Val Asn Ser Phe Leu Ser Ser Pro Phe Gln Glu Asn Trp
                290                 295                 300

Phe Leu Leu Phe Cys Arg Ile Cys Ile Tyr Leu Asn Ser Ala Ile
                305                 310                 315

Asn Pro Val Ile Tyr Asn Leu Met Ser Gln Lys Phe Arg Ala Ala
                320                 325                 330

Phe Arg Lys Leu Cys Asn Cys Lys Gln Lys Pro Thr Glu Lys Ala
                335                 340                 345

Ala Asn Tyr Ser Val Ala Leu Asn Tyr Ser Val Ile Lys Glu Ser
                350                 355                 360
```

| Asp | Arg | Phe | Ser | Thr 365 | Glu | Leu | Glu | Asp | Ile 370 | Thr | Val | Thr | Asp | Thr 375 |
|---|---|---|---|---|---|---|---|---|---|---|---|---|---|---|
| Tyr | Val | Ser | Thr | Thr 380 | Lys | Val | Ser | Phe | Asp 385 | Asp | Thr | Cys | Leu | Ala 390 |
| Ser | Glu | Asn | | | | | | | | | | | | |

PITUITARY TRH RECEPTOR

Partial funding for the research which led to the making of the present invention was provided by a grant from the National Institutes of Health. Accordingly, the United States federal government has rights to the present invention in accordance with the provisions of 35 USC §200 et seq.

Thyrotropin-releasing hormone was the first hypothalamic releasing factor to be chemically characterized. The hormone, initially isolated from the hypothalamus and thought to function solely as a releasing factor for the regulation of thyroid stimulating hormone secretion from the anterior pituitary gland, has been shown to be distributed widely throughout the central and peripheral nervous systems as well as in extraneural tissues. Receptors for this hormone have also been found in the pituitary and brain, and binding sites for thyrotropin-receptor hormone (which likely represent receptors that serve as transmembrane signaling proteins) have also been found in other tissues. The present pharmacological evidence suggests that the pituitary and brain receptors are similar but that they exhibit different isoelectric points.

Transmembrane signalling by the pituitary thyrotropin-releasing hormone receptor has been studied in detail and it has been shown that thyrotropin-releasing hormone acts via the inositol phospholipid-calcium-protein kinase C transduction pathway. Indirect evidence by Hinkle [PNASUSA 81:6183 (1984)] and Straub [J. Biol. Chem., 261:2712 (1986)] is consistent with the hypothesis that a G protein couples to the thyrotropin-releasing hormone receptor to a phospholipase C that hydrolyzes phosphatidylinositol 4,5-bisphosphate. It has, therefore, been generally assumed, therefore, that the thyrotropin-releasing hormone receptor is a member of the large family of G protein coupled receptors. However, previous attempts by others [see Johnson et al, PNASUSA 81:4227 (1984) and Phillips et al, Mol. Pharmacol. 35:533 (1989)] to purify the protein by conventional biochemical techniques have not been successful.

Thus, there is still a need to more fully understand the molecular mechanisms of thyrotropin-releasing hormone receptor signalling, the regulation of the hormone receptor number and mRNA levels under different physiological conditions, and whether different subtypes exist for the thyrotropin-releasing hormone receptor. The present invention addresses this need through the isolation of a cDNA encoding a pituitary thyrotropin-releasing hormone receptor, and describing the isolation of this cDNA and the present ligand binding and response characteristics of the receptor expressed in Xenopus oocytes and in transfected mammalian cells that demonstrate that the isolated cDNA is responsible for encoding the pituitary thyrotropin-releasing hormone receptor. More specifically, the nucleotide sequence (SEQ ID NO:1) of the thyrotropin-releasing hormone receptor, according to the present invention is as follows:

```
(SEQ ID NO: 1)
1    GAATTCCGGA GGGTTTAGAG GAACTGCCGC TCTGAAGACT GAGCCTCTGC
51   TAAGTGATCT TCCTGCCAGA CAGACTGGAC AAGATTTCTT CTGCAGGATT
101  GGAAACTTGG ACCTATTAGC ACTTCATCTA CCAGAGAAAC AGGCAGCGTG
151  ACAGAGTGAA GAGGGGAAAG AACTACTGCA AAAACAAACA GACAGAAAGG
201  TGAAGGCTGG AAAGATGTTT TAGAGTCCCC GTGTCAGAGA AGCTTCAAGC
251  CACTGAAG      ATG GAG AAT GAT ACT GTC AGT GAA ATG AAC CAA
291  ACC GAG CTC CAG CCA CAA GCA GCT GTG GCC CTC GAG TAC CAG
333  GTG GTT ACC ATC TTA CTT GTG GTC ATT ATT TGT GGA CTG GGC
375  ATT GTG GGC AAC ATC ATG GTA GTC CTG GTG GTC ATG AGA ACA
417  AAG CAC ATG AGA ACC CCT ACA AAC TGT TAC CTG GTA AGT CTG
459  GCT GTG GCA GAT CTC ATG GTT CTG GCT GCA GGA CTC CCC
501  AAC ATA ACC GAC AGT ATC TAT GGT TCC TGG GTC TAT GGC TAT
543  GTT GGC TGC CTC TGC ATT ACA TAT CTC CAG TAC CTA GGC ATT
585  AAT GCA TCT TCA TGT TCA ATA ACG GCC TTT ACC ATT GAA AGG
627  TAC ATA GCA ATC TGT CAC CCC ATC GCC CAG TTT CTC TGC
669  ACG TTT TCC AGA GCC AAA AAA ATC ATC ATC TTT GTC TGG GCC
711  TTC ACA TCC ATT TAC TGT ATG CTC TGG TTC TTC CTG CTG GAT
753  CTC AAC ATC AGC ACC TAC AAA AAC GCT GTT GTG GTT TCC TGT
795  GGC TAC AAG ATC TCC AGG AAC TAC TCA CCT ATT TAC CTA
837  ATG GAC TTT GGT GTC TTT TAT GTT GTG CCA ATG ATC CTG GCC
879  ACT GTG CTT TAT GGA TTT ATA GCT AGA ATC CTC TTC TTA AAC
921  CCC ATT CCT TCA GAC CCT AAA GAA AAC TCT AAG ATG TGG AAA
963  AAT GAC TCA ATC CAT CAG AAC AAG AAT TTG AAT TTA AAT GCC
1005 ACC AAC AGA TGC TTC AAC AGC ACT GTA TCT TCC AGG AAG CAG
1047 GTC ACC AAG ATG CTC GCA GTG GTT GTA ATT CTG TTT GCC CTT
1089 TTA TGG ATG CCC TAC AGG ACT CTT GTG GTT GTC AAC TCA TTT
1131 CTC TCC AGC CCT TTC CAG GAA AAT TGG TTC TTG CTC TTT TGC
1173 AGA ATT TGC ATT TAT CTC AAC AGT GCC ATC AAC CCA GTG ATT
1215 TAC AAC CTC ATG TCT CAG AAA TTT CGT GCA GCC TTC AGG AAG
1257 CTC TGC AAT TGC AAG CAG AAG CCC ACA GAA AAA GCT GCT AAC
1299 TAC AGT GTG GCC CTA AAT TAC AGT GTC ATC AAG GAG TCA GAC
1341 CGC TTC AGC ACA GAG CTA GAA GAT ATC ACC GTC ACC GAT ACG
1383 TAT GTG TCA ACC ACA AAA GTG TCC TTT GAT GAC ACC TGC TTG
1425 GCC TCT GAG AAC TAA    AGAAGGCCAT AAAGAACCCT ATAATGTTCT
1470 TCTGTATAT TTATTTCATA ATTATGATCT TCATCAAATA ATTCAGCAAC
1520 AGATGCTTC AGGCAAGTTA CATACTGGGA AGCAGTTCAC TATTAAGATT
1570 TTCAGCAACT TACGGACTAC ATCAAGTGAC AAGTTAACC TATGGTGTGA
1620 GAACTTAATT CAAAACTCAA ATAATCTTCT TTGACAAGAG TGATCATGGA
1670 TAAAAATGGA CTCAGTTCTT GTGCATATAG CTTTTCTTTG ACTGCCAAAC
1720 AAGAGCGAAT ATGAACTTCC ATCTTGAACT GG — 3'
```

The nucleotide sequence has been deposited into Genbank, accession number M37490.

More specifically, the thyrotropin-releasing hormone receptor is obtained from the instructions contained in the genetic codons beginning with nucleotide 259 and ending with nucleotide 1439 (SEQ ID NO:2), or more specifically the following:

(SEQ ID NO: 2)

```
259       ATG GAG AAT GAT ACT GTC AGT GAA ATG AAC CAA
291  ACC GAG CTC CAG CCA CAA GCA GCT GTG GCC CTC GAG TAC CAG
333  GTG GTT ACC ATC TTA CTT GTG GTC ATT ATT TGT GGA CTG GGC
375  ATT GTG GGC AAC ATC ATG GTA GTC CTG GTG GTC ATG AGA ACA
417  AAG CAC ATG AGA ACC CCT ACA AAC TGT TAC CTG GTA AGT CTG
459  GCT GTG GCA GAT CTC ATG GTT CTG GTG GCT GCA GGA CTC CCC
501  AAC ATA ACC GAC AGT ATC TAT GGT TCC TGG GTC TAT GGC TAT
543  GTT GGC TGC CTC TGC ATT ACA TAT CTC CAG TAC CTA GGC ATT
585  AAT GCA TCT TCA TGT TCA ATA ACG GCC TTT ACC ATT GAA AGG
627  TAC ATA GCA ATC TGT CAC CCC ATC AAA GCC CAG TTT CTC TGC
669  ACG TTT TCC AGA GCC AAA AAA ATC ATC ATC TTT GTC TGG GCC
711  TTC ACA TCC ATT TAC TGT ATG CTC TGG TTC CTG CTG GAT
753  CTC AAC ATC AGC ACC TAC AAA AAC GCT GTT GTG GTT TCC TGT
795  GGC TAC AAG ATC TCC AGG AAC TAC TAC TCA CCT ATT TAC CTA
837  ATG GAC TTT GGT GTC TTT TAT GTT GTG CCA ATG ATC CTG GCC
879  ACT GTG CTT TAT GGA TTT ATA GCT AGA ATC CTC TTC TTA AAC
921  CCC ATT CCT TCA GAC CCT AAA GAA AAC TCT AAG ATG TGG AAA
963  AAT GAC TCA ATC CAT CAG AAC AAG AAT TTG AAT TTA AAT GCC
1005 ACC AAC AGA TGC TTC AAC AGC ACT GTA TCT TCC AGG AAG CAG
1047 GTC ACC AAG ATG CTC GCA GTG GTT GTA ATT CTG TTT GCC CTT
1089 TTA TGG ATG CCC TAC AGG ACT CTT GTG GTC AAC TCA TTT
1131 CTC TCC AGC CCT TTC CAG GAA AAT TGG TTC TTG CTC TTT TGC
1173 AGA ATT TGC ATT TAT CTC AAC AGT GCC ATC AAC CCA GTG ATT
1215 TAC AAC CTC ATG TCT CAG AAA TTT CGT GCA GCC TTC AGG AAG
1257 CTC TGC AAT TGC AAG CAG AAC CCC ACA GAA AAA GCT GCT AAC
1299 TAC AGT GTG GCC CTA AAT TAC AGT GTC ATC AAG GAG TCA GAC
1341 CGC TTC AGC ACA GAG CTA GAA GAT ATC ACC GTC ACC GAT ACG
1383 TAT GTG TCA ACC ACA AAA GTG TCC TTT GAT GAC ACC TGC TTG
1425 GCC TCT GAG AAC TAA
```

The deduced amino acid sequences (SEQ ID NO:3) of the thyrotropin-releasing hormone receptor, beginning at the nucleotide 259, according to the present invention is as follows:

(SEQ ID NO: 3)

| | | | | | | | | | | | | | | |
|---|---|---|---|---|---|---|---|---|---|---|---|---|---|---|
| Met 1 | Glu | Asn | Asp | Thr 5 | Val | Ser | Glu | Met | Asn 10 | Gln | Thr | Glu | Leu | Gln 15 |
| Pro | Gln | Ala | Ala | Val 20 | Ala | Leu | Glu | Tyr | Gln 25 | Val | Val | Thr | Ile | Leu 30 |
| Leu | Val | Val | Ile | Ile 35 | Cys | Gly | Leu | Gly | Ile 40 | Val | Gly | Asn | Ile | Met 45 |
| Val | Val | Leu | Val | Val 50 | Met | Arg | Thr | Lys | His 55 | Met | Arg | Thr | Pro | Thr 60 |
| Asn | Cys | Tyr | Leu | Val 65 | Ser | Leu | Ala | Val | Ala 70 | Asp | Leu | Met | Val | Leu 75 |
| Val | Ala | Ala | Gly | Leu 80 | Pro | Asn | Ile | Thr | Asp 85 | Ser | Ile | Tyr | Gly | Ser 90 |
| Trp | Val | Tyr | Gly | Tyr 95 | Val | Gly | Cys | Leu | Cys 100 | Ile | Thr | Tyr | Leu | Gln 105 |
| Tyr | Leu | Gly | Ile | Asn 110 | Ala | Ser | Ser | Cys | Ser 115 | Ile | Thr | Ala | Phe | Thr 120 |
| Ile | Glu | Arg | Tyr | Ile 125 | Ala | Ile | Cys | His | Pro 130 | Ile | Lys | Ala | Gln | Phe 135 |
| Leu | Cys | Thr | Phe | Ser 140 | Arg | Ala | Lys | Lys | Ile 145 | Ile | Ile | Phe | Val | Trp 150 |
| Ala | Phe | Thr | Ser | Ile 155 | Tyr | Cys | Met | Leu | Trp 160 | Phe | Phe | Leu | Leu | Asp 165 |
| Leu | Asn | Ile | Ser | Thr 170 | Tyr | Lys | Asn | Ala | Val 175 | Val | Val | Ser | Cys | Gly 180 |
| Tyr | Lys | Ile | Ser | Arg 185 | Asn | Tyr | Tyr | Ser | Pro 190 | Ile | Tyr | Leu | Met | Asp 195 |
| Phe | Gly | Val | Phe | Tyr 200 | Val | Val | Pro | Met | Ile 205 | Leu | Ala | Thr | Val | Leu 210 |
| Tyr | Gly | Phe | Ile | Ala 215 | Arg | Ile | Leu | Phe | Leu 220 | Asn | Pro | Ile | Pro | Ser 225 |
| Asp | Pro | Lys | Glu | Asn 230 | Ser | Lys | Met | Trp | Lys 235 | Asn | Asp | Ser | Ile | His 240 |
| Gln | Asn | Lys | Asn | Leu 245 | Asn | Leu | Asn | Ala | Thr 250 | Asn | Arg | Cys | Phe | Asn 255 |
| Ser | Thr | Val | Ser | Ser 260 | Arg | Lys | Gln | Val | Thr 265 | Lys | Met | Leu | Ala | Val 270 |
| Val | Val | Ile | Leu | Phe 275 | Ala | Leu | Leu | Trp | Met 280 | Pro | Tyr | Arg | Thr | Leu 285 |
| Val | Val | Val | Asn | Ser 290 | Phe | Leu | Ser | Ser | Pro 295 | Phe | Gln | Glu | Asn | Trp 300 |
| Phe | Leu | Leu | Phe | Cys 305 | Arg | Ile | Cys | Ile | Tyr 310 | Leu | Asn | Ser | Ala | Ile 315 |

-continued

| | | | | | | | | | | | | |
|---|---|---|---|---|---|---|---|---|---|---|---|---|
| Asn | Pro | Val | Ile | Tyr 320 | Asn | Leu | Met | Ser | Gln 325 | Lys | Phe | Arg | Ala | Ala 330 |
| Phe | Arg | Lys | Leu | Cys 335 | Asn | Cys | Lys | Gln | Lys 340 | Pro | Thr | Glu | Lys | Ala 345 |
| Ala | Asn | Tyr | Ser | Val 350 | Ala | Leu | Asn | Tyr | Ser 355 | Val | Ile | Lys | Glu | Ser 360 |
| Asp | Arg | Phe | Ser | Thr 365 | Glu | Leu | Glu | Asp | Ile 370 | Thr | Val | Thr | Asp | Thr 375 |
| Tyr | Val | Ser | Thr | Thr 380 | Lys | Val | Ser | Phe | Asp 385 | Asp | Thr | Cys | Leu | Ala 390 |
| Ser | Glu | Asn | *** | | | | | | | | | | |

This protein has a predicted molecular weight of 44.5 kilodaltons. Hydropathy analysis using the Kyte and Doolittle [see J Mol Biol 157:105 (1982)] and Eisenberg [see Science 245:510 (1989)] algorithms predicts seven transmembrane domains, in general agreement with the topology proposed for other G protein coupled receptors. Two potential N-linked glycosylation sites with the N-X-, T/S consensus sequence are presented in the N-terminus at positions 3 and 10. Two cysteines homologous to those in the $\beta_2$ receptor that have been proposed to engage in a disulfide bond [see Biochemistry 29:2335 (1990)] are present in extracellular loops 2 (Cys-98) and 3 (Cys-179). These residues may also form a disulfide bond in the thyrotropin releasing hormone receptor (TRH-R) since it has been shown that thyrotropin releasing hormone (TRH) binding is markedly reduced when disulfide bonds are disrupted [see J Neurochem 42:209 (1984)]. A cysteine present in the C-terminus close to transmembrane domain M-VII (Cys-335) is homologous to the cysteine that may be acylated by palmitic acid in the $\beta_2$ receptor [see J Biol Chem 264:7564 (1989)]. Fifteen of the last 52 amino acids are either serine or threonine, potential sites for regulatory phosphorylation. Candidates for phosphorylation by protein kinase C include three residues in intracellular loop 3 (Thr-250, Ser-259, and Ser-260) and four in the C-terminus (Ser-324, Thr-342, Ser-360, and Thr-379). The third intracellular loop has been shown to be important in coupling to G proteins [see Raymond, Hnatowich, Caron & Lefkowitz, in *ADP-Ribosylating Toxins and G Proteins*, American Society for Microbiology, Washington, D. C. pp. 163–188 (1990)]. In the TRH-R, amino acids 227-235 may be predicted to form an amphipathic helix, a secondary structure which may be necessary for G protein activation.

Proteins which in bacteriorhodopsin impart bends to the transmembrane helices are present in M-V, M-VI and M-VII, however there is no proline in M-IV. Most receptors in this family have prolines in all four final transmembrane domains; the TSh receptor, LH-HCG receptor, and mas-encoded protein do not. M-III does not contain Asp which has been shown to be necessary for agonist binding to the $\beta$ receptor, and is present in all adrenergic, muscarinic, serotonin and dopamine receptors, but absent in the visual opsins, mas-encoded protein, and TSH, LH-HCG, substance K and substance P receptors. Likewise, the TRH-R does not contain the serines in M-V which have been proposed to interact with the hydroxyl groups of ligands that contain a catechol moiety.

When the mouse TRH-R amino acid sequence according to the present invention was used to search the Genpept (Genbank) and Swiss-Prot (EMBL) databases, the results indicated significant sequence identity with only some of those receptors proposed to couple to G proteins. When the transmembrane domains only are compared, the percent identity is as follows: rat substance P receptor 21.5%, octopus rhodopsin 24.1%, rat serotonin type 2 receptor 29.4%, turkey $\beta_1$ receptor 28.9%, putative dog thyroid receptor RDC8 28%, rat dopamine $D_2$ receptor 32.5%, rat muscarinic M5 receptor 28.8%, and human $\alpha_2$ receptor 29.5%. Analysis of the significance or these sequence identities with the Pearson program RDF2 confirmed that these receptors share common ancestry and also that the mouse TRH-R is much less related to other receptors such as the dog TSH receptor, pig LH-HCG receptor, rat mas-encoded protein, yeast A factor, Dictyostelium cAMP receptor, and pHS1-2.

The following examples, detailed description of the present invention and various figures are provided in order to provide the reader with a more complete understanding of the present invention. However, it is to be understood that the following examples are provided only for their general content and are not to be taken as limitations of the present invention as defined in this description or the appended claims.

In the figures:

FIG. 1 is a depiction of the elecgrophysiological responses to TRH in *Xenopus oocytes*;

FIG. 4 depicts the effect of antisense TRH-R RNA on the acquired TRH and carbachol responses in *Xenopus oocytes*;

FIG. 5 depicts the antisense inhibition of the TRH but not the carbachol response;

More specifically, and as will be described in greater detail in the following description of the present invention, FIG. 1 is a depiction of the electophysiological responses to TRH in *Xenopus oocytes* which have been injected 48 hours previously with 20 ng of sucrose gradient fractionated TtT poly(A) RNA (FIG. 1A), 2 ng of RNA transcribed in vitro from the TRH receptor cDNA (pBSmTRHR) (FIG. 1B), or 20 ng of RNA transcribed from a different clone taken from the same cDNA library (FIG. 1C).

Figure 2:
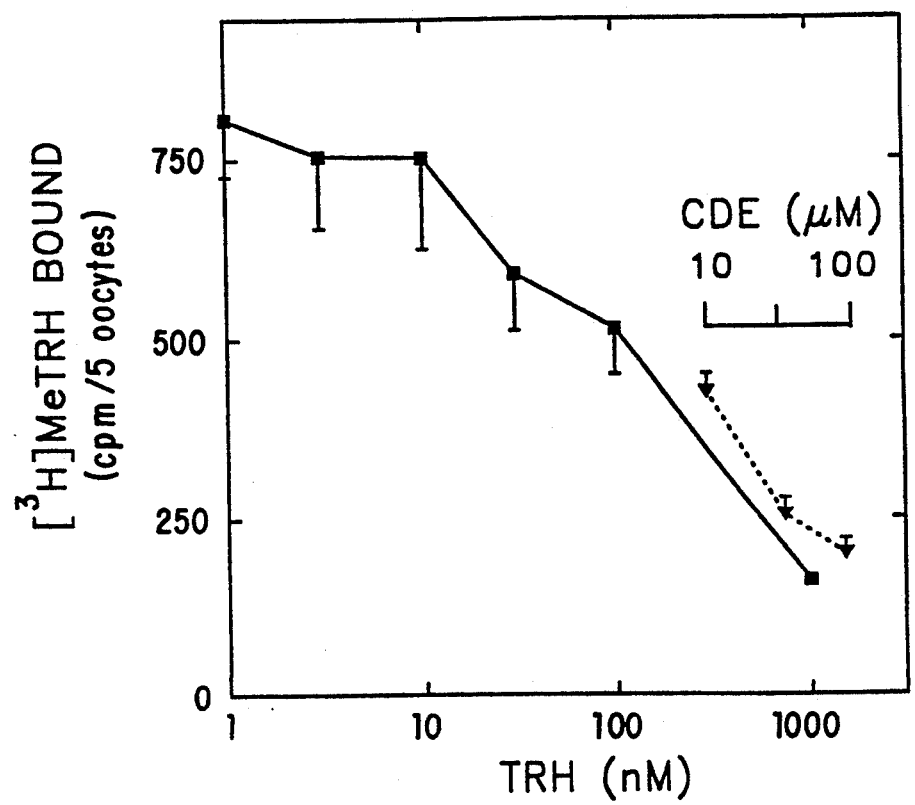
FIG. 2 is a depiction of the expression of TRH-Rs in *Xenopus oocytes* injected with RNA transcribed in vitro from the plasmid containing the TRH-R cDNA (pBSmTRHR)

FIG. 2 depicts TRH (the filled squares) and chlordiazepoxide (the unfilled circles) competion for the binding of [$^3$H]methylTRH to oocytes expressing TRH receptors 3 days after injection of 5 ng of in vitro transcribed RNA. The results are presented in this figure as mean ± S.E. of duplicate determinations.

Figure 3:
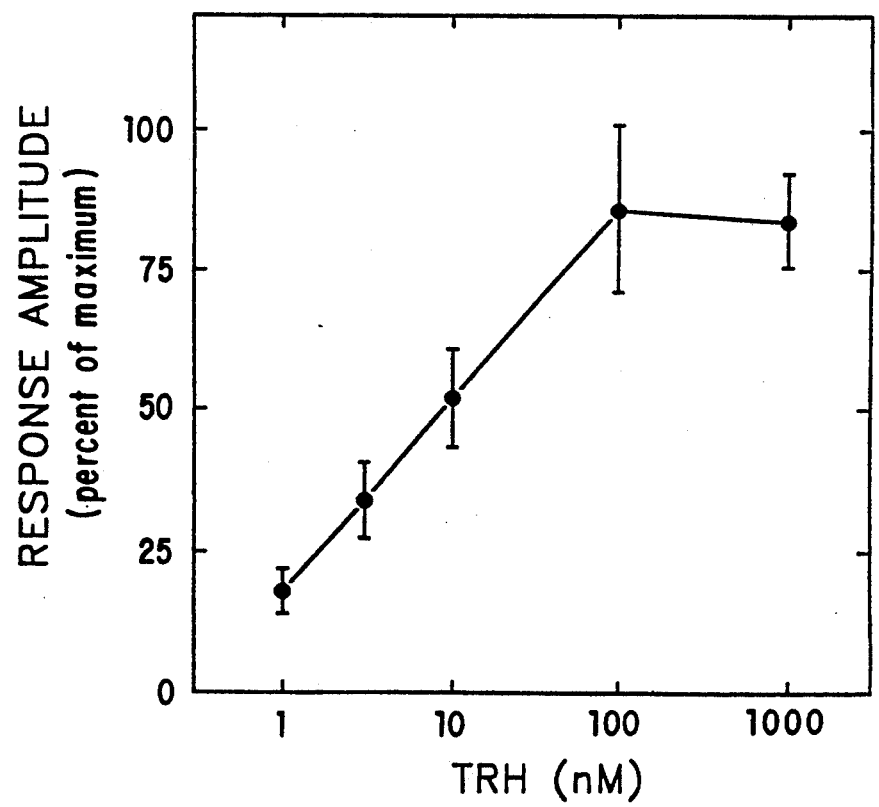
FIG. 3 is a similar depiction of the expression of TRH-Rs in *Xenopus oocytes* injected with RNA transcribed in vitro from the plasmid containing the TRH-R cDNA (pBSmTRHR)

FIG. 3 more specifically depicts the concentration-response relationship of Xenopus oocytes 3 days following injection of 5 ng of in vitro transcribed RNA. In FIG. 3, the results are presented from two experiments with $N \geq 6$.

FIG. 4 depicts the results of an experiment wherein 5 ng of antisense RNA transcribed in vitro from a plasmid Bluescript containing a portion of the TRH-R cDNA (pBSmTRHR1.8) was incubated for 1 hour with 300 ng oligo-dt of RNA isolated from normal rat pituitary glands. The mixture was then injected into oocytes and electrophysiological responses to 1 μM TRH were assayed 3 days later. Depictions of representative responses in the absence (FIG. 4A) or presence (FIG. 4B) of antisense TRH-R RNA.

The antisense inhibition of the TRH, but not the carbachol response, are presented in FIG. 5. The depiction presented is taken from duplicate experiments with $N \geq 6$.

Figure 6:
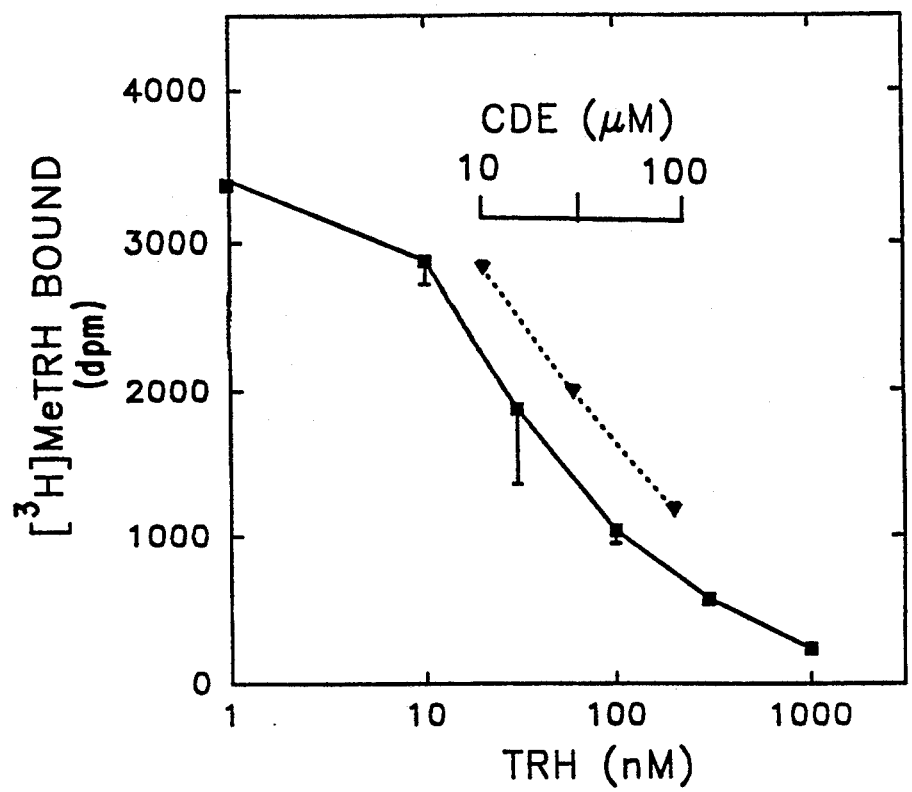
FIG. 6 depicts the expression of TRH-Rs in COS-1 cells transfected with pCDM8mTRHR.
Figure 7:
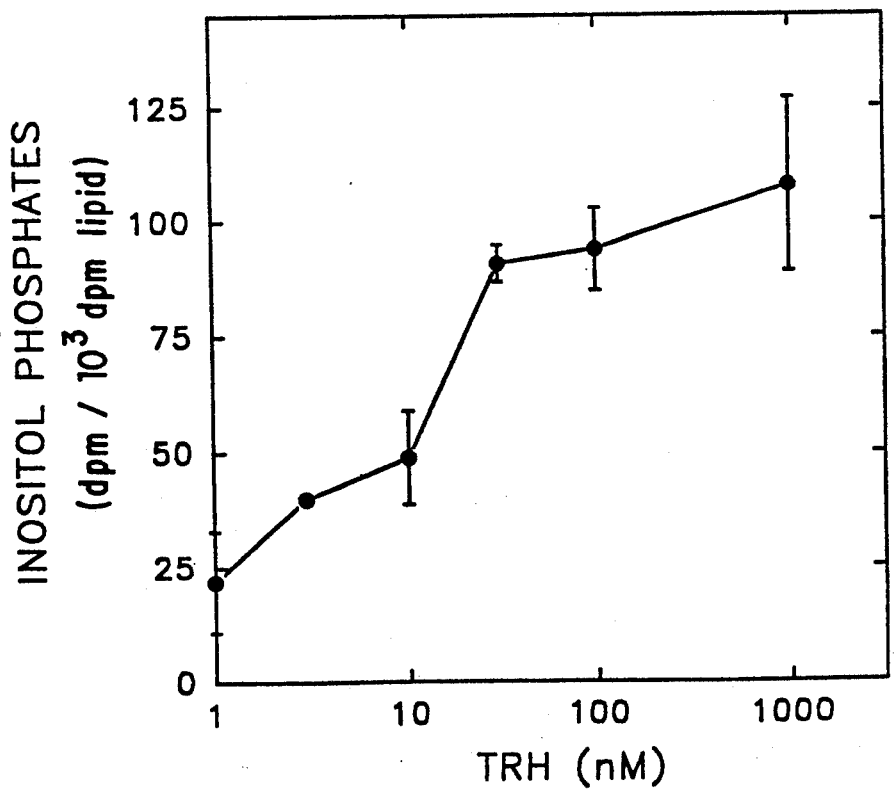
FIG. 7 depicts a stimulation of inositol phosphate formation by TRH.

In FIGS. 6 and 7, COS-1 cells were transfected with the TRH-R cDNA according to the present invention, in the mammalian expression vector pCDM8 (pCDM8m TRHR) and assayed for binding and responses 48 hours later. Specifically, FIG. 6, depicts the TRH (filled squares) and chlordiazepoxide (unfilled circles) competition for the binding of [$^3$H]methylTRH. COS-1 cells transfected with pCDM8mTRHR were assayed for the binding of [$^3$H]methylTRH in the presence of increasing amounts of either unlabeled TRH or chlordiazepoxide. Results are presented as mean ± range of data from duplicate determinations in one of two similar experiments. In FIG. 7, COS-1 cells transfected with pCDM8mTRHR were labeled with myo-[$^3$H]inositol for 48 hours, washed, and tested for dose-dependent stimulation of inositol phosphate production by TRH. The results are presented as mean ± S.D. of triplicate determinations from one of two similar experiments.

A directional, size-selected cDNA library was constructed using the method as reported by Frech and Joho [Gene Anal. Techn. 6:33 (1989)]. Poly(A) RNA isolated from a mouse pituitary thyrotropic (TtT) tumor and size-fractioned on a sucrose gradient. The fraction which gave the highest specific TRH-H mRNA activity when injected into stage 5 or 6 Xenopus laevis oocytes [see Science 238:1406 (1987) and Molecular Endocrinology 1:918 (1987)] was used for preparative cDNA synthesis. To find an enzyme which would generate the highest yield of long cDNAs, seven lots of murine leukemia virus reverse transcriptase from four commercial sources was compared, using RNA fractions from the sucrose gradient adjacent to the one with the highest specific TRH-R mRNA activity as test templates. A typical response evoked by a maximally effective dose of TRH (1 μM) in voltage clamped oocytes after injection of 20 ng of size fractioned TtT poly(A) RNA is depicted in FIG. 1(a). cDNAs of between 3 and 5 kilobases were purified by agarose gel electrophoresis and electroelution using conventional techniques.

The size-selected cDNAs were ligated directionally into λZAP (Stratagene) such that transcription using T7 RNA polymerase would yield sense RNA. A library of $1.2 \times 10^6$ clones was constructed that was greater than 95% recombinant. The primary library was immediately divided and amplified individually in 60 sublibraries of approximately 20,000 clones each. λ DNA was prepared by the CTAB-DNA precipitation method [see Biotechniques 7:514 (1989)]. More specifically, the construction of a size-selected, directional cDNA library was prepared in accordance with the following example.

EXAMPLE 1

Eleven micrograms of thyrotropic tumor RNA from sucrose gradient fraction No. 19 was mixed with 5 μg primer in 40 μl of Tris-HCl (pH 7.5), heated for 1 minute to 70° C., and cooled to room temperature. First strand synthesis was performed in a volume of 100 μl containing 50 mM Tris-HCl (pH 8.3), 75 mM KCl, 3 mM MgCl$_2$, 10 mM DTT, 1 mM dNTPs, 0.1 mg/ml bovine serum albumin, 1600 U/ml of RNasin (Promega), and 2000 units of MMLV reverse transcriptase (BRL). After incubation at 37° C. for 2 hours, the reaction was used directly for second strand synthesis in a final volume of 400 μl containing 50 mM Tris-HCl (pH 8.0), 20 mM KCl, 10 mM MgCl$_2$, 10 mM DTT, 0.25 mM dNTPs, 25 μl bovine serum albumin, and 10 μCi of α-$^{32}$P-CTP. Synthesis was initiated with 8 units of RNAase H (Amersham) and 170 units of E. coli DNA polymerase I (New England Biolabs). The reaction was incubated for 60 minutes at 12° C., for 60 minutes at room temperature, and then heated for 10 minutes at 70° C. Twenty units of T4 DNA polymerase (Boehringer Mannheim) was added and the reaction was incubated for 15 minutes at 37° C. Five μl was removed and second strand synthesis was quantitated by TCA precipitation of DNA onto glass filters. The second strand was calculated to be 4.5 μg, and if, as usual, the second strand yield was quantitative, then incorporation of dCTP into the first strand was 40.9%. The mixture was adjusted to 10 mM EDTA, 0.5% SDS, and then extracted sequentially with equal volumes of phenol, phenol/chloroform, and chloroform, and finally precipitated with 100 mM NaCl and ethanol.

Eighty percent of the double-stranded cDNA (7.2 μg) was dissolved in 200 μl of 30 mM sodium acetate (ph 5.0), 50 mM NaCl, 1 mM ZnCl$_2$, and 5% glycerol containing 27 units of mung bean nuclease (Promega). The reaction was incubated for 60 minutes at 30° C., and the DNA was extracted and precipitated as above. To assure blunt ends, the DNA was subjected to a second polymerase reaction in 100 μl of 50 mM Tris-HCl (pH 8.0), 15 mM (NH$_4$)$_2$SO$_4$, 10 mM MgCl$_2$, 0.1 EDTA, 10 mM DTT, 0.2 mM dNTPs, 0.2 mg/ml bovine serum albumin, and 10 units of T4 polymerase for 30 minutes at 37° C. The DNA was extracted and precipitated as above. The recovery was 89.5% (6.84 μg) based on Cherenkov scintillation counting and a correction for radioactive decay.

Methylation of Eco RI sites was done in 40 μl of 0.1 mM Tris-HCl (ph 8.0), 0.1 mM NaCl, 1 mM EDTA, 10 mM DTT, 80 μM S-adenosylmethionine, 0.1 mg/ml bovine serum albumin, and 80 units of Eco RI (New England Biolabs). The mixture was incubated for 60 minutes at 37° C. Another 80 units of enzyme was added and the incubation was continued for another 60 minutes. After extraction and precipitation, recovery was 88% (6.04 μg). The DNA was dissolved in 20 μl of 50 mM Tris-HCl (pH 7.5), 10 mM MgCl$_2$, 10 mM DTT, 1 mM ATP, 50 μg/ml bovine serum albumin, and 15% PEG 8000 containing 2 μg of Eco RI linkers [d(pCCGGAATTCCGG)] and 2 units of T4 DNA ligase (Boehringer Mannheim). The mixture was incubated at 16° C. for 14 hours. After addition of NaCl to a final concentration of 100 mM, the ligase was inactivated by incubation for 15 minutes at 68° C. The mixture was extracted and precipitated with 2M ammonium acetate and ethanol. The recovery was 93% (5.64 μg). The DNA was sequentially digested at 37° C. (2 hours each incubation) with 68 units of Not I twice and then with 240 units of Eco RI twice. The mixture was extracted and ethanol precipitated without further addition of salt. The recovery was 95% (5.4 μg).

The cDNA was fractioned on a 1% TAE agarose gel containing 0.5 μg/ml ethidium bromide and visualized by long wave ultraviolet light. cDNAs ranging fro 3 to 5 kilobases were purified from the gel slice by electroelution for 3 hours at 150 V constant voltage using an Eurtrap TM electroelution apparatus (Schleicher and Scheull). Electroelution was quantitative based on Cherenkov scintillation counting of the gel slice before and after elution. The elute was extracted and precipitated with 100 mM NaCl. The recovery was 671 ng (12.4%).

Test ligations of a portion of the size-fractionated cDNA to λZAP that was modified to contain cohesive ends for Eco RI and Not I were performed to determine the optimal ratio of insert to vector. The preparative ligation reaction (10 μl) contained 75 ng of size-fractionated cDNA, 500 ng of modified λZAP, 50 mM Tris-HCl (pH 7.5). 10 mM $MgCl_2$, 10 mM DTT, 1 mM ATP, 50 mg/ml bovine serum albumin, and 0.5 units of T4 DNA ligase. The reaction was incubated for 16 hours at 14° C. Aliquots of the ligation mixture were packaged directly using the Gigapack Gold packaging extract (Stratagene) according to the manufacturer's recommendations, and the packaged phage was titered using E. coli strain BB4 (Stratagene). A library of $1.2 \times 10^6$ clones was constructed. Based on the ratio of colorless to blue plaques on NZY plates containing 10 mM IPTG (isopropyl-β-D-thiogalactopyranoside) and 5 mg/ml X-gal (5-bromo-4-chloroindolyl-β-D-galactopyranoside), the library was >95% recombinant. The primary library was immediately divided into 60 pools of approximately $2 \times 10^4$ clones each, and each pool was amplified individually overnight on 150 mm NZY plates.

λ Phage DNA was prepared from individual plate lysates from 20 of the 60 pools of $2 \times 10^4$ clones by the CTAB-DNA precipitation method. The yield was usually 15 to 25 μg of phage DNA per 150 mm plate. A portion of each plate lysate was kept as a stock for further division and amplification.

The DNA was digested with Not I, proteinase K treated, extracted and precipitated. In vitro transcription of sense RNA was carried out by a modification of the procedure used in cloning the serotonin type 1c receptor, and more fully described in the following example.

EXAMPLE 2

The DNA (15-25 μg) from Example 1 was digested overnight at 37° C. with 5 U/μg Not I, treated with 100 μg/ml proteinase K at 37° C. for 30 minutes, and extracted and precipitated with 300 mM sodium acetate and ethanol. In vitro transcription of sense RNA was carried out using the reported method used in cloning the serotonin 5-$HT_{1c}$ receptor. The following reagents were combined at room temperature in a volume of 50 μl: 40 mM Tris-HCl (pH 7.5), 50 mM NaCl, 8 mM $MgCl_2$, 2 mM spermidine, 10 mM DTT, 1.25 μg/μl bovine serum albumin, 2000 U/ml RNasin (Promega), 0.5 mM UTP, CTP, and ATP, and 0.2 mM GTP, 1 mM GpppG and 70 units of T7 RNA polymerase (Pharmacia). The reaction was incubated for 2 hours at 40° C., extracted, precipitated with 2.5M ammonium acetate and ethanol, and resuspended in 10 μl 100 mM KCl. The usual yield was between 3 and 8 Mg of RNA as quantitated by addition of 2 μCi per reaction of $\alpha$-$^{32}$P-UTP followed by TCA precipitation of an aliquot of RNA onto glass filters.

Transcripts (15–40 ng/oocyte) from 20 pools of 20,000 clones each were injected individually int Xenopus oocytes, and two or three days later the oocytes were placed under a voltage clamp and 1μμ TRH administered in the bath. As depicted in FIG. 1(b), RNA transcribed in vitro from a single clone isolated by serial division of this library conferred responsiveness to TRH; responses were also obtained from injection of as little as 1 pg of TNA transcripts; RNA transcribed from any other individual clone isolated from the remaining 19 pools did not confer TRH responsivity as depicted in FIG. 1(c). The positive pool of 20,000 clones was reduced by dilution to pools of 2000, 200, 30, 10, and finally a single positive clone (λZAPPmTRHR) was isolated which contained a 3.8 kb cDNA insert, and as described, both strands of the 5' most 1752 bp were sequenced.

The plasmid Bluescript (pBSmTRHR) was excision rescued from the TRH-R λZAP clone prepared above, by coinfection with helper phage R-408. Restriction fragments of the cDNA were subcloned into M13mp19 utilizing known techniques, and the resultant was sequenced by the dideoxy chain termination method of Sanger.

Xenopus oocytes were injected with 5 ng of sense RNA transcripts ans assayed for specific binding of TRH and electrophysiological responses to TRH. Binding to intact oocytes was performed as described in the literature [see Molecular Endocrinology 3:9070 (1989)], using 2 nM [$^3$H]methylTRH as the labeled ligand, and unlabeled TRH and chlordiazepoxide as competitive inhibitors. More specifically, these processes were done as described in the following example.

EXAMPLE 3

Adult Xenopus laevis females were maintained at a 12/12 hour light/dark cycle at 18° C. Ovary fragments were excised under sterile conditions and oocytes defolliculated by a 1 to 3 hour treatment with collagenase (1.5-3 mg/ml, Sigma) in OR-2 medium without $Ca^{+2}$. Oocytes were maintained at 20° C. in OR-2E media.

A single oocyte, in a 0.4 ml perfusion chamber, was impaled with two standard glass electrodes filed with 3M KCl and maintained under voltage clamp using a Dagan 8500 intracellular clamp. Drugs were included in the perfusate and applied at a flow rate of 8 ml/min. The apparent latency is the time between achieving greater than 80% of the perfusate concentration in the perfusion chamber (5.5 sec after switching to TRH) and the initial deflection of the pen on the chart recorder due to membrane depolarization.

Intracellular injections were performed with a third electrode, with a tip manually broken to 0.5-3 uM diameter and back-filed with the desired solution. The volume of injection (25-50 nL) was verified by injecting a drop of the solution into oil and measuring the diameter with a reticle-equipped microscope. The volume was controlled by electronic timer and pressure adjustment and did not exceed 0.5% of the oocyte volume.

GH$_3$ cell RNA was prepared according to published protocols. RNA from TtT tumors was prepared by homogenizing the tumors (15-20 grams) in guanidinium thiocyanate solution and centrifuging at 5000×g for 20 minutes at 4° C. RNA from the suspension below the lipid layer was isolated by centrifugation through a 10 ml 5.7M CaCl$_2$-100 mM EDTA cushion. The RNA pellet was washed with 80% ethanol, dissolved in water, reprecipitated with ethanol and re-dissolved in water. Poly(A) RNA was prepared and, in some experiments, was fractionated on a sucrose density gradient.

RNA was injected (25-50 nl) at the equator of oocytes, and responses were tested 24 to 72 hours after injection.

Five to 10 oocytes were incubated at 4° C. in 0.2 ml OR-2 containing 40 nm [$^3$H]methylTRH without or with 1 μl unlabeled TRH for up to 3 hours. Oocytes were washed 7 times with 4 ml ice-cold OR-2 solution and radioactivity measured by liquid scintillation counting. Specific binding was calculated by subtracting radioactivity bound in the presence from that in the absence of unlabeled TRH. Nonspecific binding was between 30 and 45% of total binding.

The electrophysiological response to TRH was measured in separate experiments. Analysis of the ligand binding and dose-response characteristics of the receptor expressed in oocytes after injection of RNA transcribed in vitro from pBSmTRTH demonstrated that the cDNA according to the present invention encodes a functional TRH-R. Inhibition of the binding of [$^3$H]methylTRH, an analog with 10-fold higher affinity than TRH for the pituitary TRH-R [see Neuroendocrinology 32:310 (1981)], by TRH and by chlordiazepoxide, a competitive antagonist of TRH binding in the pituitary [see Endocrinology 119:833 (1986)], is illustrated in FIG. 2. The apparent inhibition constants (K$_i$) for TRH and chlordiazepoxide were calculated to be approximately 30 nM and 3 μM, respectively. These values are close to those reported for TRH receptors in GH$_3$ pituitary cells.

The concentration-dependency of the TRH-induced oocyte electrophysiological response is shown in FIG. 3. As mentioned above, as little as 1 nM TRH evoked a response, half-maximal responses were observed with 10 nM TRH, and maximum responses with 100 nM TRH. This dose dependency is the same as that observed in GH$_3$ cells when rapid effects of TRH, such as generation of inositol 1,4,5-triphosphate or elevation of cytoplasmic calcium, were measured [see J Biol Chem 261:2712 (1986) and J Biol Chem 259:5827 (1984)].

To ascertain if the cloned mouse TRH-R sequence is similar to endogenous rat pituitary TRH-R mRNA, and thereby give an indication of whether the cDNA clone of the present invention may be used to isolate cDNA clones for related proteins, a study was performed to determine whether antisense RNA transcribed in vitro from a portion of the TRH-R cDNA in plasmid Bluescript (pBSmTRHR1.8) would inhibit TRH-R expression in oocytes injected with RNA isolated from normal rat anterior pituitary glands. In this series of experiments, *Xenopus oocytes* were injected with 5 ng of sense RNA transcripts and assayed for specific binding of TRH and electrophysiological responses to TRH. Binding to intact oocytes were performed using 2 nM [$^3$H]methylTRH as the labeled ligand and unlabeled TRH and chlordiazepoxide as competitive inhibitors. Injection of RNA isolated from normal rat pituitaries led to acquisition of responses to TRH and carbachol, a muscarinic agonist (see FIG. 4(A)); there were no intrinsic responses to TRH or carbachol in uninjected collagenase-treated oocytes. In FIG. 4(B), responses from an oocyte injected with RNA from normal rat pituitaries that had been incubated with antisense TRH-R RNA is depicted. The TRH response in the oocyte was abolished, but the carbachol response was not affected. As shown in the compilation of data in FIG. 5, when antisense RNA was allowed to hybridize to rat pituitary RNA prior to injection, the response to TRH was inhibited by 87%, whereas the response to carbachol was not significantly inhibited.

In order to examine both ligand binding and response characteristics of the cloned receptor in mammalian systems, the entire TRH-R cDNA, according to the present invention, contained in a Not I/HindIII fragment was cloned directly into the eukaryotic expression vector pCDM8 (pCDM8TRHR) that contains the CMV promoter (pCDM8mTRHR) [see Nature 329:840 (1987)]. COS-1 cells were transfected using the DEAE dextran method, and after 48 to 72 hours the cells were assayed for [$^3$H]methylTRH binding and TRH stimulated inositol phosphate formation. This protocol is more specifically described in the following example.

EXAMPLE 4

On the day prior to transfection, 35 mm, 6 well tissue culture plates were seeded with 6×10$^5$ in DMEM with 10% FCS; cells should be just subconfluent for transfection. A transfection cocktail was prepared: supercoiled plasmid DNA (ethanol precipitated if necessary) was resuspended in 0.3 ml PBS, and then vortexed. 0.1 ml DEAE-dextran was added to bring the final concentration to 0.5 mg/ml, and the solution mixed thoroughly. The tissue culture medium was aspirated from the cell cultures and the COS cells were rinsed twice with 2 ml of PBS warmed to 37° C. The PBS was aspirated, the transfection cocktail was added gently to the side of each well in the tissue culture plate, and the cocktail was distributed evenly by tilting the plate. The plates were incubated at 37° C. for 30 minutes with gentle rocking every 10 minutes to prevent drying. Two ml of DMEM containing 10% FCS and 80 uM chloroquine was added to each well and the plates allowed to incubate for an additional 2.5 hours at 37° C. Following incubation, the medium was aspirated and replaced with 1 ml of DMEM containing 10% FCS and 10% DMSO. After 2.5 minutes, the medium was aspirated and 2 ml of fresh DMEM containing 10% FCS was added. The cells were assayed 48-72 hours following transfection.

No specific binding or TRH stimulated inositol phosphate formation was detectable in untransfected COS-1 cells or cells transfected with pCDM8 alone. As depicted in FIG. 6, [$^3$H]methylTRH binding and displacement by TRH and chlordiazepoxide were measured. The K$_3$'s for TRH (10 nM) and for chlordiazepoxide (20 μM) agree with those found in both oocytes injected with RNA transcribed in vitro from pBSmTRHR (FIG. 2) and in GH$_3$ cells [see Endocrinology 119:833 (1986)]. TRH-stimulated inositol phosphate formation is shown in FIG. 7. TRH exhibited an EC$_{50}$ of approximately 10 nM, which is similar to that found in oocytes injected with RNA transcribed in vitro from pBSmTRHR (FIG. 3) and in GH$_3$ cells [see J Biol Chem 259:5827 (1984)].

In conclusion, the thyroid-releasing hormone is an important extracellular regulatory molecule that functions as a releasing factor in the anterior pituitary gland and as a neurotransmitter/neuromodulator in the central and peripheral nervous systems. Binding sites for the hormone are present in these tissues but prior to the making of the present invention, thyroid-releasing hormone receptor has not been purified from any source.

Using *Xenopus laevis* oocytes in an expression cloning strategy, the present invention describes the first successful isolation of a novel cDNA clone which encodes the pituitary thyroid-releasing receptor. In addition, using the cDNA clone according to the present invention, the preceding description has shown that (1) injection of sense RNA transcribed in vitro from the cDNA according to the present invention into *Xenopus oocytes* leads to the expression of cell-surface receptors which bind thyrotropin-releasing hormone, and the competitive antagonist, chlordiazepoxide, with appropriate affinities and that elicit electrophysiological responses to the hormone with the appropriate concentration-dependency; (2) antisense RNA inhibits the thyrotropin-releasing hormone response in *Xenopus oocytes* which have been injected with RNA isolated from normal anterior pituitary glands; and (3) that transfection of COS-1 cells with this cDNA leads to expression of receptors which bind thyrotropin-releasing hormone and chlordiazepoxide with appropriate affinities and that transduce thyrotropin-releasing hormone stimulation of inositol phosphate formation.

As is known, cDNA clones for one protein may be used to isolate cDNA clones for related proteins from libraries. In this manner, the TRH receptor cDNA of the present invention may be used to isolate cDNAs for the gonadotropin-releasing hormone (luteinizing-hormone releasing hormone) receptor, and the growth hormone releasing hormone receptor among others. Once isolated, these cDNA could then be used to develop, for example, anti-fertility and growth stimulating drugs, respectively. Another application of the present invention would be to isolate related receptors for neurotrophic factors as TRH has effects in the central and peripheral nervous systems. Once isolated, drugs could then be developed that may, for example, enhance nerve cell regeneration.

Thus while we have illustrated and described the preferred embodiment of our invention, it is to be understood that this invention is capable of variation and modification and we therefore do not wish to be limited to the precise terms set forth, but desire to avail ourselves of such changes and alterations which may be made for adapting the invention to various usages and conditions. Among such variations and modifications are, for example, minor insertions and deletions in either the the cDNA or amino acid sequences which result in no untoward effects upon the activity of the modified nucleotide or peptide from that of the depicted sequences; substitutions in the nucleic acid sequence which result in the same or substantially the same peptide; substitutions in the nucleic acid which result in the same or substantially the same activity as that found in the peptide having the sequence given; muteins; mutations; and all other modifications of the amino acid and nucleic acid sequences which do not change the activity of the nucleotide or protein according to the present invention. Accordingly, such changes and alterations are properly intended to be within the full range of equivalents, and therefore within the purview of the following claims.

Having thus described our invention and the manner and process of making and using it in such full, clear, concise, and exact terms so as to enable any person skilled in the art to which it pertains, or with it is most nearly connected, to make and use the same,

We claim:

1. A cDNA molecule encoding a thyrotropin-releasing hormone receptor wherein the cDNA molecule essentially contains the following sequence:

1 GAATTCCGGA GGGTTTAGAG GAACTGCCGC

TCTGAAGACT GAGCCTCTGC

51 TAAGTGATCT TCCTGCCAGA CAGACTGGAC

AAGATTTCTT CTGCAGGATT

101 GGAAACTTGG ACCTATTAGC ACTTCATCTA

CCAGAGAAAC AGGCAGCGTG

151 ACAGAGTGAA GAGGGGAAAG AACTACTGCA

AAAACAAACA GACAGAAAGG

201 TGAAGGCTGG AAAGATGTTT TAGAGTCCCC

GTGTCAGAGA AGCTTCAAGC

251 CACTGAAG ATG GAG AAT GAT ACT

GTC AGT GAA ATG AAC CAA

291 ACC GAG CTC CAG CCA CAA GCA GCT

GTG GCC CTC GAG TAC CAG

333 GTG GTT ACC ATC TTA CTT GTG GTC

ATT ATT TGT GGA CTG GGC

375 ATT GTG GGC AAC ATC ATG GTA GTC

CTG GTG GTC ATG AGA ACA

417 AAG CAC ATG AGA ACC CCT ACA AAC

TGT TAC CTG GTA AGT CTG

459 GCT GTG GCA GAT CTC ATG GTT CTG

GTG GCT GCA GGA CTC CCC

501 AAC ATA ACC GAC AGT ATC TAT GGT

TCC TGG GTC TAT GGC TAT

543 GTT GGC TGC CTC TGC ATT ACA TAT

CTC CAG TAC CTA GGC ATT

585 AAT GCA TCT TCA TGT TCA ATA ACG

GCC TTT ACC ATT GAA AGG

627 TAC ATA GCA ATC TGT CAC CCC ATC

AAA GCC CAG TTT CTC TGC

669 ACG TTT TCC AGA GCC AAA AAA ATC

ATC ATC TTT GTC TGG GCC

711 TTC ACA TCC ATT TAC TGT ATG CTC

TGG TTC TTC CTG CTG GAT

753 CTC AAC ATC AGC ACC TAC AAA AAC

GCT GTT GTG GTT TCC TGT

795 GGC TAC AAG ATC TCC AGG AAC TAC

TAC TCA CCT ATT TAC CTA

837 ATG GAC TTT GGT GTC TTT TAT GTT

GTG CCA ATG ATC CTG GCC

879 ACT GTG CTT TAT GGA TTT ATA GCT

AGA ATC CTC TTC TTA AAC

921 CCC ATT CCT TCA GAC CCT AAA GAA

AAC TCT AAG ATG TGG AAA

963 AAT GAC TCA ATC CAT CAG AAC AAG

AAT TTG AAT TTA AAT GCC

1005 ACC AAC AGA TGC TTC AAC AGC ACT

GTA TCT TCC AGG AAG CAG

1047 GTC ACC AAG ATG CTC GCA GTG GTT

GTA ATT CTG TTT GCC CTT

1089 TTA TGG ATG CCC TAC AGG ACT CTT

GTG GTT GTC AAC TCA TTT

1131 CTC TCC AGC CCT TTC CAG GAA AAT

TGG TTC TTG CTC TTT TGC

1173 AGA ATT TGC ATT TAT CTC AAC AGT

GCC ATC AAC CCA GTG ATT

1215 TAC AAC CTC ATG TCT CAG AAA TTT

CGT GCA GCC TTC AGG AAC

1257 CTC TGC AAT TGC AAG CAG AAG CCC

ACA GAA AAA GCT GCT AAC

1299 TAC AGT GTG GCC CTA AAT TAC AGT

GTC ATC AAG GAG TCA GAC

1341 CGC TTC AGC ACA GAG CTA GAA GAT

ATC ACC GTC ACC GAT ACG

1383 TAT GTG TCA ACC ACA AAA GTG TCC

TTT GAT GAC ACC TGC TTG

1425 GCC TCT GAG AAC TAA AGAAGGCCAT

AAAGAACCCT ATAATGTTCT

1470 TCATGTATAT TTATTTCATA ATTATGATCT

TCATCAAATA ATTCAGCAAC

```
1520 AGATGTCTTC AGGCAAGTTA CATACTGGGA

AGCAGTTCAC TATTAAGATT

1570 TTCAGCAACT TACGGACTAC ATCAAGTGAC

AAGTTTAACC TATGGTGTGA

1620 GAACTTAATT CAAAACTCAA ATAATCTTCT

TTGACAAGAG TGATCATGGA

1670 TAAAAATGGA CTCAGTTCTT GTGCATATAG

CTTTTCTTTG ACTGCCAAAC

1720 AAGAGCGAAT ATGAACTTCC ATCTTGAACT

GG — 3'.
```

2. A cDNA molecule encoding pituitary thyrotropin-releasing hormone receptor wherein the cDNA molecule essentially contains the following nucleotide sequence:

```
259  ATG GAG ATT GAT ACT
         GTC AGT GAA ATG AAC CAA
291  ACC GAG CTC CAG CCA CAA GCA GCT
         GTG GCC CTC GAG TAC CAG
333  GTG GTT ACC ATC TTA CTT GTG GTC
         ATT ATT TGT GGA CTG GGC
375  ATT GTG GGC AAC ATC ATG GTA GTC
         CTG GTG GTC ATG AGA ACA
417  AAG CAC ATG AGA ACC CCT ACA AAC
         TGT TAC CTG GTA AGT CTG
459  GCT GTG GCA GAT CTC ATG GTT CTG
         GTG GCT GCA GGA CTC CCC
501  AAC ATA ACC GAC AGT ATC TAT GGT
         TCC TGG GTC TAT GGC TAT
543  GTT GGC TGC CTC TGC ATT ACA TAT
         CTC CAG TAC CTA GGC ATT
585  AAT GCA TCT TCA TGT TCA ATA ACG
         GCC TTT ACC ATT GAA AGG
627  TAC ATA GCA ATC TGT CAC CCC ATC
         AAA GCC CAG TTT CTC TGC
669  ACG TTT TCC AGA GCC AAA AAA ATC
         ATC ATC TTT GTC TGG GCC
711  TTC ACA TCC ATT TAC TGT ATG CTC
         TGG TTC TTC CTG CTG GAT
753  CTC AAC ATC AGC ACC TAC AAA AAC
         GCT GTT GTG GTT TCC TGT
795  GGC TAC AAG ATC TCC AGG AAC TAC
         TAC TCA CCT ATT TAC CTA
837  ATG GAC TTT GGT GTC TTT TAT GTT
         GTG CCA ATG ATC CTG GCC
879  ACT GTG CTT TAT GGA TTT ATA GCT
         AGA ATC CTC TTC TTA AAC
921  CCC ATT CCT TCA GAC CCT AAA GAA
         AAC TCT AAG ATG TGG AAA
963  AAT GAC TCA ATC CAT CAG AAC AAG
         AAT TTG AAT TTA AAT GCC
1005 ACC AAC AGA TGC TTC AAC AGC ACT
         GTA TCT TCC AGG AAG CAG
1047 GTC ACC AAG ATG CTC GCA GTG GTT
         GTA ATT CTG TTT GCC CTT
1089 TTA TGG ATG CCC TAC AGG ACT CTT
         GTG GTT GTC AAC TCA TTT
1131 CTC TCC AGC CCT TTC CAG GAA AAT
         TGG TTC TTG CTC TTT TGC
1173 AGA ATT TGC ATT TAT CTC AAC AGT
         GCC ATC AAC CCA GTG ATT
1215 TAC AAC CTC ATG TCT CAG AAA TTT
         CGT GCA GCC TTC AGG AAG
1257 CTC TGC AAT TGC AAG CAG AAG CCC
         ACA GAA AAA GCT GCT AAC
1299 TAC AGT GTG GCC CTA AAT TAC AGT
         GTC ATC AAG GAG TCA GAC
1341 CGC TTC AGC ACA GAG CTA GAA GAT
         ATC ACC GTC ACC GAT ACG
1383 TAT GTG TCA ACC ACA AAA GTG TCC
         TTT GAT GAC ACC TGC TTG
1425 GCC TCT GAG AAC TAA.
```

3. A peptide having thyrotropin-releasing hormone receptor activity and having an amino acid sequence consisting of:

```
Met Glu Asn Asp Thr Val Ser Glu Met Asn Gln Thr Glu Leu Gln
 1           5                    10                    15

Pro Gln Ala Ala Val Ala Leu Glu Tyr Gln Val Val Thr Ile Leu
                20                    25                    30

Leu Val Val Ile Ile Cys Gly Leu Gly Ile Val Gly Asn Ile Met
                35                    40                    45
```

-continued

| | | | | | | | | | | | | | |
|---|---|---|---|---|---|---|---|---|---|---|---|---|---|
|Val|Val|Leu|Val|Val 50|Met|Arg|Thr|Lys|His 55|Met|Arg|Thr|Pro|Thr 60|
|Asn|Cys|Tyr|Leu|Val 65|Ser|Leu|Ala|Val|Ala 70|Asp|Leu|Met|Val|Leu 75|
|Val|Ala|Ala|Gly|Leu 80|Pro|Asn|Ile|Thr|Asp 85|Ser|Ile|Tyr|Gly|Ser 90|
|Trp|Val|Tyr|Gly|Tyr 95|Val|Gly|Cys|Leu|Cys 100|Ile|Thr|Tyr|Leu|Gln 105|
|Tyr|Leu|Gly|Ile|Asn 110|Ala|Ser|Ser|Cys|Ser 115|Ile|Thr|Ala|Phe|Thr 120|
|Ile|Glu|Arg|Tyr|Ile 125|Ala|Ile|Cys|His|Pro 130|Ile|Lys|Ala|Gln|Phe 135|
|Leu|Cys|Thr|Phe|Ser 140|Arg|Ala|Lys|Lys|Ile 145|Ile|Ile|Phe|Val|Trp 150|
|Ala|Phe|Thr|Ser|Ile 155|Tyr|Cys|Met|Leu|Trp 160|Phe|Phe|Leu|Leu|Asp 165|
|Leu|Asn|Ile|Ser|Thr 170|Tyr|Lys|Asn|Ala|Val 175|Val|Val|Ser|Cys|Gly 180|
|Tyr|Lys|Ile|Ser|Arg 185|Asn|Tyr|Tyr|Ser|Pro 190|Ile|Tyr|Leu|Met|Asp 195|
|Phe|Gly|Val|Phe|Tyr 200|Val|Val|Pro|Met|Ile 205|Leu|Ala|Thr|Val|Leu 210|
|Tyr|Gly|Phe|Ile|Ala 215|Arg|Ile|Leu|Phe|Leu 220|Asn|Pro|Ile|Pro|Ser 225|
|Asp|Pro|Lys|Glu|Asn 230|Ser|Lys|Met|Trp|Lys 235|Asn|Asp|Ser|Ile|His 240|
|Gln|Asn|Lys|Asn|Leu 245|Asn|Leu|Asn|Ala|Thr 250|Asn|Arg|Cys|Phe|Asn 255|
|Ser|Thr|Val|Ser|Ser 260|Arg|Lys|Gln|Val|Thr 265|Lys|Met|Leu|Ala|Val 270|
|Val|Val|Ile|Leu|Phe 275|Ala|Leu|Leu|Trp|Met 280|Pro|Tyr|Arg|Thr|Leu 285|
|Val|Val|Val|Asn|Ser 290|Phe|Leu|Ser|Ser|Pro 295|Phe|Gln|Glu|Asn|Trp 300|
|Phe|Leu|Leu|Phe|Cys 305|Arg|Ile|Cys|Ile|Tyr 310|Leu|Asn|Ser|Ala|Ile 315|
|Asn|Pro|Val|Ile|Tyr 320|Asn|Leu|Met|Ser|Gln 325|Lys|Phe|Arg|Ala|Ala 330|
|Phe|Arg|Lys|Leu|Cys 335|Asn|Cys|Lys|Gln|Lys 340|Pro|Thr|Glu|Lys|Ala 345|
|Ala|Asn|Tyr|Ser|Val 350|Ala|Leu|Asn|Tyr|Ser 355|Val|Ile|Lys|Glu|Ser 360|
|Asp|Arg|Phe|Ser|Thr 365|Glu|Leu|Glu|Asp|Ile 370|Thr|Val|Thr|Asp|Thr 375|
|Tyr|Val|Ser|Thr|Thr 380|Lys|Val|Ser|Phe|Asp 385|Asp|Thr|Cys|Leu|Ala 390|
|Ser|Glu|Asn|***| | | | | | | | | | | |

\* \* \* \* \*